United States Patent

D'Adamo

Patent Number: 5,639,969
Date of Patent: Jun. 17, 1997

[54] BALL TESTING APPARATUS AND METHOD

[76] Inventor: Bruce D'Adamo, One Rose Terrace, Chatham, N.J. 07928

[21] Appl. No.: 602,868

[22] Filed: Jan. 29, 1996

[51] Int. Cl.$^6$ .................................................. G01N 3/08
[52] U.S. Cl. ............................... 73/818; 73/790; 73/81
[58] Field of Search .............................. 73/81, 85, 790, 73/818, 819, 862.391, 862.451

[56] References Cited

U.S. PATENT DOCUMENTS

| 2,628,496 | 2/1953 | Wick | 73/818 |
|---|---|---|---|
| 3,470,737 | 10/1969 | Fridley | 73/818 |
| 3,665,757 | 5/1972 | Hoag | 73/818 |
| 4,313,289 | 2/1982 | Birdsong, Jr. | 73/818 |
| 4,876,658 | 10/1989 | Hass | 364/550 |
| 5,222,391 | 6/1993 | Reenstra | 73/81 |
| 5,245,862 | 9/1993 | Zeiss | 73/79 |
| 5,291,774 | 3/1994 | Putman | 73/82 |
| 5,511,410 | 4/1996 | Sherts | 73/81 |

Primary Examiner—George M. Dombroske
Assistant Examiner—Max H. Noori
Attorney, Agent, or Firm—LaMorte & Associates

[57] ABSTRACT

A portable ball testing device for testing inflated sport balls such as tennis balls, racquet balls and the like that includes a tubular element with an entrance port and an exit port that are sized to enable the a ball to be placed within and removed from the respective ports of the tubular element. A restricted region is disposed within the tubular element between the entrance port and the exit port. A ramrod element is provided that extends into the tubular element. A ram head is provided at the end of the ramrod element within the tubular element. As the ramrod element is advanced into the tubular element, the ram head abuts against the ball and pushes the ball through the restricted region. A handle is coupled to the ramrod element via a spring. When a manual force is applied to the handle, the spring compresses and the force is transferred to the ramrod element by the spring. A gauge is provided between the handle and the ramrod element that provides a visual indication as to the compression experienced by the spring. A threshold level is indicated on the gauge that indicated whether or not the force needed to advance the ball through the restricted region surpasses a predetermined threshold.

14 Claims, 2 Drawing Sheets

BALL TESTING APPARATUS AND METHOD

BACKGROUND OF THE INVENTION

1. Field of the Invention

The present invention relates to devices and methods used to test the compressibility of sporting balls, such as tennis balls, racquet balls and the like. More specifically, the present invention relates to a portable handheld device that can be used by a player to determine the condition of a ball prior to the start of the game.

2. Description of the Prior Art

Under the rules of the American Tennis Association, tennis balls are manufactured to specific tolerances, thereby reducing the role of the ball as a variable during play. Specifically, a tennis ball should have a forward deformation between 0.22 inches and 0.29 inches and a return deformation of between 0.35 inches and 0.425 inches when experiencing an eighteen pound load. During manufacture, tennis balls are typically tested in large complex machines such as the Stevens deflectometer, invented by Percy Stevens and patented in Great Britain under Patent No. 230,250. Other such complex testing machines are exemplified by U.S. Pat. No. 4,876,658 to Hass, entitled METHOD AND APPARATUS FOR SYSTEMATICALLY TESTING OBJECTS INCLUDING TENNIS BALLS, which is assigned to the United States Tennis Association.

The use of such complex machines during manufacture does ensure that most tennis balls purchased by players meet the proper design specifications. However, as every player knows, tennis balls do not last forever. As a tennis ball is repeatedly struck, the ball deforms. After a while, the cycles of deformation permanently effect the ball, causing the tennis ball to become soft. The softening of the tennis ball is progressive. As a result, it is common that a ball may become too soft after only a few games. As the ball falls below accepted tolerances, play is effected because the ball does not bounce as high as would be expected or rebound off the tennis racket as quickly as would be expected. A need therefore exists for a means that would enable a player to test the "softness" of a ball before or between games in a match, thereby eliminating any defective ball before the ball adversely effects the play of the game.

In the prior art, there have been several devices invented that are intended to test the softness of a tennis ball. Such prior art devices are exemplified by U.S. Pat. No. 5,291,774 to Putnam, entitled TENNIS BALL TESTER and U.S. Pat. No. 5,222,391 to Reenstra also entitled TENNIS BALL TESTER. However, both of these prior art references have undesirable features. The Putnam device is large and bulky and is unlikely to be carried in a player's tennis bag. The Reenstra device is electric and uses an electronic pressure sensor and control circuitry that adds greatly to the cost and complexity of the device.

It is therefore an object of the present invention to provide a tennis ball testing device that is inexpensive, light weight, easy to use and rapid to use.

It is a further object of the present invention to provide a method of testing a tennis ball that is inexpensive to execute and rapid to perform.

These objects are fulfilled by the present invention as described and claimed below.

SUMMARY OF THE INVENTION

The present invention is a portable ball testing device for testing inflated sport balls such as tennis balls, racquet balls and the like. The ball testing device includes a tubular element with an entrance port and an exit port that are sized to enable a ball to be placed within and removed from the respective ports of the tubular element. A restricted region is disposed within the tubular element between the entrance port and the exit port. The restricted region defines an opening within the tubular element that is smaller than the diameter of the ball. As a result, the ball must be deformed by a predetermined degree in order to pass through the restricted region. A ramrod element is provided that extends into the tubular element. A ram head is provided at the end of the ramrod element within the tubular element. As the ramrod element is advanced into the tubular element, the ram head abuts against the ball and pushes the ball through the restricted region.

The force used to advance the ramrod element and the ram head is manually applied. A handle is coupled to the ramrod element via a spring. As a result, when a manual force is applied to the handle, the spring compresses and the force is transferred to the ramrod element by the spring. The greater the force applied to the handle, the greater the compression of the spring and the greater the force applied through the ramrod element to the ball. A gauge is provided between the handle and the ramrod element that provides a visual indication as to the compression experienced by the spring. A threshold level is marked on the gauge that indicates whether or not the force needed to advance the ball through the restricted region surpasses a predetermined threshold. If the force needed to advance the ball does not surpass the threshold, the ball has tested to be too soft for regulation play.

BRIEF DESCRIPTION OF THE DRAWINGS

For a better understanding of the present invention, reference is made to the following description of two exemplary embodiments thereof, considered in conjunction with the accompanying drawings, in which.

DETAILED DESCRIPTION OF THE INVENTION

Although the present invention device can be used to test many types of balls, such as racquet balls, handballs, squash balls and the like, the present invention is particularly well adapted for use in testing tennis balls. As a result, the present invention will be described in an application for testing tennis balls in order to set forth the best mode contemplated for the device.

Figure 1:
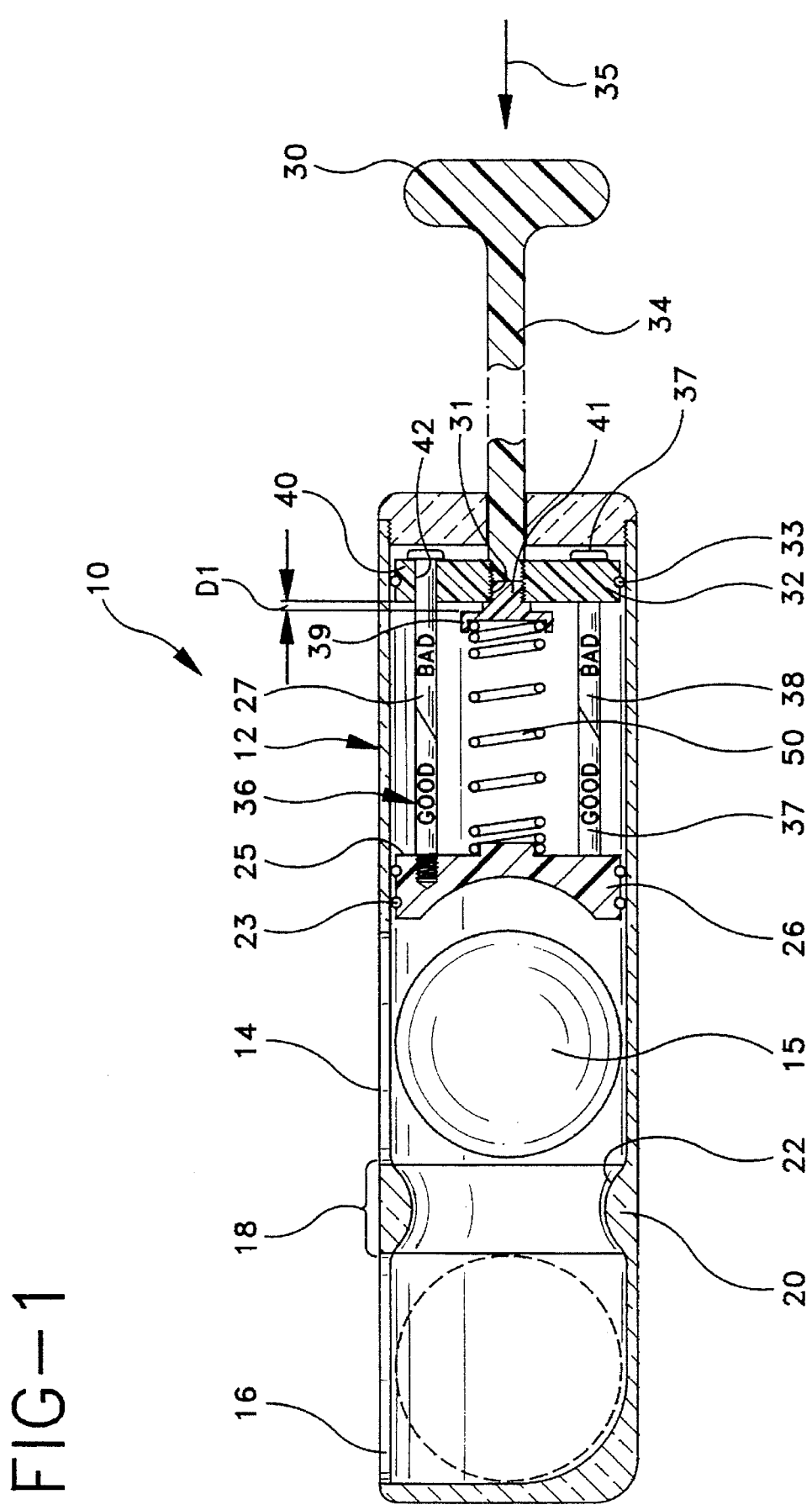
FIG. 1 is a cross-sectional view of a first preferred embodiment of the present invention ball testing device, shown in conjunction with a tennis ball.

Referring to FIG. 1, a first preferred embodiment of the present invention ball tester device 10 is shown. The ball tester device 10 includes a tubular element 12 with an interior diameter generally large enough to accommodate the diameter of the ball being tested. In the preferred embodiment, the tubular element 12 is made of a transparent material so that a user can view the interior of the tubular element 12. However, in alternate embodiments the tubular body can be opaque or can embody only one small transparent section that enables the interior of the tubular element to be viewed.

Two access ports 14, 16 are formed in the tubular element 12. The access ports 14, 16 are sized to enable the test ball 15 to be placed within, and removed from, the interior of the tubular element 12. Although the tubular element 12 is generally uniform in shape, there exists a restricted region 18 on the interior of the tubular element 12 where the internal diameter of the tubular element 12 decreases between 5% and 33%. In the shown embodiment, the restricted region 18 is created by the presence of an annular protrusion 20 that extends inwardly from the interior surface of the tubular element 12. However, it should be understood that many other obstruction configurations can be used. The annular protrusion 20 selected has a sloping lead surface 22 that gradually constricts the internal diameter of the tubular element 12 within the restricted region 18.

The purpose of the present invention ball tester device 10 is to determine how soft a test ball is by measuring how much force is required to compress the ball by a predetermined amount. The softer the ball is, the easier it will be to compress the ball. If the ball is too soft, it is rejected as being bad. In the embodiment shown in FIG. 1, the test ball 15 is placed into the tubular element 12 through the first access port 14. Within the tubular element 12 is a ram head 26 capable of reciprocally moving back and forth within the tubular element 12. At least one O-ring 23 is disposed around the periphery of the ram head 26, wherein the O-ring 23 contacts the interior surface of the tubular element 12. The presence of the O-ring 23 enables the ram head 26 to move freely back and forth down the center of the tubular element 12, yet prevents the ram head 26 from moving laterally away from the longitudinal axis of the tubular element 12.

As the ram head 26 advances within the tubular element 12, the ram head 26 pushes the test ball 15 into the restricted region 18. The test ball 15 is compressed as it rides up the sloping lead surface 22 of the annular protrusion 20. As the test ball 15 becomes more and more compressed, the force needed to advance the test ball 15 through the restricted region 18 increases. As the test ball 15 passes the restricted region 18, the test ball 15 again returns to its uncompressed shape, wherein the test ball 15 can be removed through the second access port 16. The present invention ball tester device 10 works by measuring the maximum resistance force that the test ball applies to the ram head 26, as the ram head 26 pushes the test ball 15 through the restricted region 18. If the maximum resistance force fails to surpass a predetermined threshold value, the test ball 15 fails the test and can be rejected as "bad".

As a person skilled in the art will recognize, there are many ways to drive a ram head in a cylinder and measure the maximum resistance force experienced by the ram head. For example, a ram head can be driven pneumatically, hydraulically or by an electric motor. In a pneumatic application, an electronic sensor could monitor the maximum air pressure needed to drive the ram head. In a hydraulic application, an electronic sensor could monitor the maximum fluid pressure needed to drive the ram head. If an electric motor were used, the electric load of the motor could be monitored, thereby indicating the maximum force applied by the motor. Many such ram head drive systems exist in the art of presses and can be incorporated into the present invention.

In the embodiment of FIG. 1, a manually driven mechanical means is used to drive the ram head 26 and measure the maximum resistance experienced by the ram head 26. The use of such a manual system makes the overall ball testing device 10 low cost, lightweight and easy to operate. In the shown embodiment, a handle 30 is provided that is coupled to a push plate 32 by a rigid rod 34. The push plate 32 is a rigid plate having a threaded central aperture 31. The push plate 32 is sized so that it is capable of reciprocally moving within the confines of the tubular element 12. An O-ring 33 is disposed around the periphery of the push plate 32, wherein the O-ring 33 contacts the interior surface of the tubular element 12. The presence of the O-ring 33 enables the push plate 32 to move freely back and forth down the center of the tubular element 12, yet prevents the push plate 32 from moving laterally away from the longitudinal axis of the tubular element 12.

The rigid rod 34 that extends from the handle 30 terminates in a reduced threaded region 41 at the end opposite the handle 30. The threaded region 41 passes through the threaded aperture 31 in the center of the push plate 32. A spring receptacle 39 is attached to the end of the threaded region 41 on the rigid rod 34. The spring receptacle 39 is sized to receive the end of a coil spring 50. Since the threaded region 41 engages the threaded aperture 31 in the center of the push plate 32, it will be understood that the distance D1 between the spring receptacle 39 and the push plate 32 can be selectively varied by rotating the rigid rod 34 with respect to the push plate 32. Furthermore, it will be understood that any manual force applied to the handle 30 in the direction of arrow 35 will cause the push plate 32 to move in the direction of arrow 35.

A plurality of guide rods 36 extend outwardly from the rear surface 25 of the ram head 26. The guide rods 36 are parallel and are rigidly affixed to the ram head 26. A gauge indicia 27 is printed on each of the guide rods 20 36. The gauge indicia 27 preferably includes a green colored section 37 marked "GOOD" and a red colored section 38 marked "BAD". The green colored section 37 and the red colored section 38 overlap, thereby providing a region that is both "GOOD" and "BAD" to some changing degree. In the preferred embodiment, the gauge indicia 27 on each of the guide rods 36 is not the same. Rather, the scale of the "GOOD" regions and the "BAD" regions are different to provide different scale references for a purpose which will later be explained.

Apertures 40 are disposed in the push plate 32. Each of the apertures 40 is lined with soft bearings 42 or an equivalent component. The guide rods 36 that extend from the ram head 26 pass through each bearings 42, wherein each of the guide rods 36 terminate on the far side of the push plate 32 with an enlarged head 37. The guide rods 36 are free to move across the bearings 42. As a result, the push plate 32 is free to move reciprocally along the length of the guide rods 36. The use of soft bearings 42 helps protect the guide rods 36 and prevents the gauge indicia 27 from being worn off the guide rods 36.

A spring 50 is disposed between the ram head 26 and the spring receptacle 39 at the end of the rigid rod 34. The spring 50 biases the ram head 26 away from the spring receptacle 39 and consequently biases the ram head 26 away from the push plate 32. As a result, the push plate 32 is biased against the enlarged heads 37 of the guide rods 36. As the spring receptacle 39 is adjusted away from the push plate 32, the distance D1 between the spring receptacle 39 and the push plate 32 increases. This causes the spring 50 to become more compressed, thereby controlling the degree of the bias that pushes the push plate 32 against the enlarged heads 37 of the guide rods 36.

As the handle 30 is pushed in the direction of arrow 35, the spring receptacle 39 compresses the spring 50. Simultaneously, the push plate 32 is forced to travel within the tubular element 12. The push plate 32 slides down along the length of guide rods 36 towards the ram head 26. The compression of the spring 50 acts upon the ram head 26 and drives the ram head 26 along the length of the tubular element 12. The movement of the ram head 26 pushes the test ball 15 along the length of the tubular element 12 until the test ball 15 engages the sloping lead surface 22 of the annular protrusion 20 and begins to become compressed. As the test ball 15 is pushed farther into the restricted region 18, the resistance offered by the test ball 15 increases. As a result, a greater force must be applied to the handle 30 to continue to advance the ram head 26. As the force on the handle 30 is increased, the spring 50 becomes more compressed between the ram head 26 and the spring receptacle 39. This causes the push plate 32 to slide down along the guide rods 36, thereby exposing a portion of the gauge indicia 27 on the guide rods 36 above the push plate 32. The amount by which the guide rods 36 extent above the push plate 32 acts as a gauge that can be viewed by the person testing the test ball 15.

In tennis, balls often have different knapping (i.e. felt coverings), either do to different manufactures or do to wear. In the embodiment of the present invention ball testing device 10 shown, three guide rods 36 are used, wherein each of the guide rods contains a different gauge indicia 27. The three gauge indicia 27 are used for three different knap conditions respectively, wherein one gauge indicia is for smooth knapping, one gauge indicia is for normal knapping and one gauge indicia is for a large or rough knapping. The spring constant of the spring 50 and the size of the restricted region 18 are selected so that if a good test ball 15 is in the tubular element 12, the spring 50 will be nearly compressed before the ram head 26 drives the test ball 15 through the restricted region 18. As the spring 50 approaches full compression, the push plate 32 would be very near the ram head 26 and nearly all of the guide rods 36, corresponding to the test ball's knap type, would extend up beyond the push plate 32. Since the degree by which the guide rods 36 extend beyond the push plate 32 is proportional to the degree of resistance offered by the test ball 15, the push plate 32 acts as a gauge indicator. If the green colored "GOOD" section of the appropriate guide rod 36 extends beyond the push plate 32, then a user knows that the test ball 15 is not too soft and is good for play. However, if only the red colored "BAD" section of the guide rod 36 extends passed the push plate 32, then it can be determined that the test ball 15 is too soft and is not good for play.

As has been previously explained, the distance D1 between the spring receptacle 39 and the push plate 32 can be selectively adjusted by rotating the threaded region 41 of the rigid rod 34 within the threaded aperture 31 of the push plate 32. This adjustability controls the initial compression and bias force offered by the spring 50. The adjustability of the initial compression of the spring 50 enables the present invention ball testing device 10 to be "zeroed" for the type of test ball 15 being used. As a result, the overall ball testing device 10 can be adjusted, as needed, to provide accurate test results. The adjustability of the spring 50 also enables the ball testing device 10 to be calibrated as the spring 50 grows old and the bias force offered by the spring 50 changes.

Figure 2:
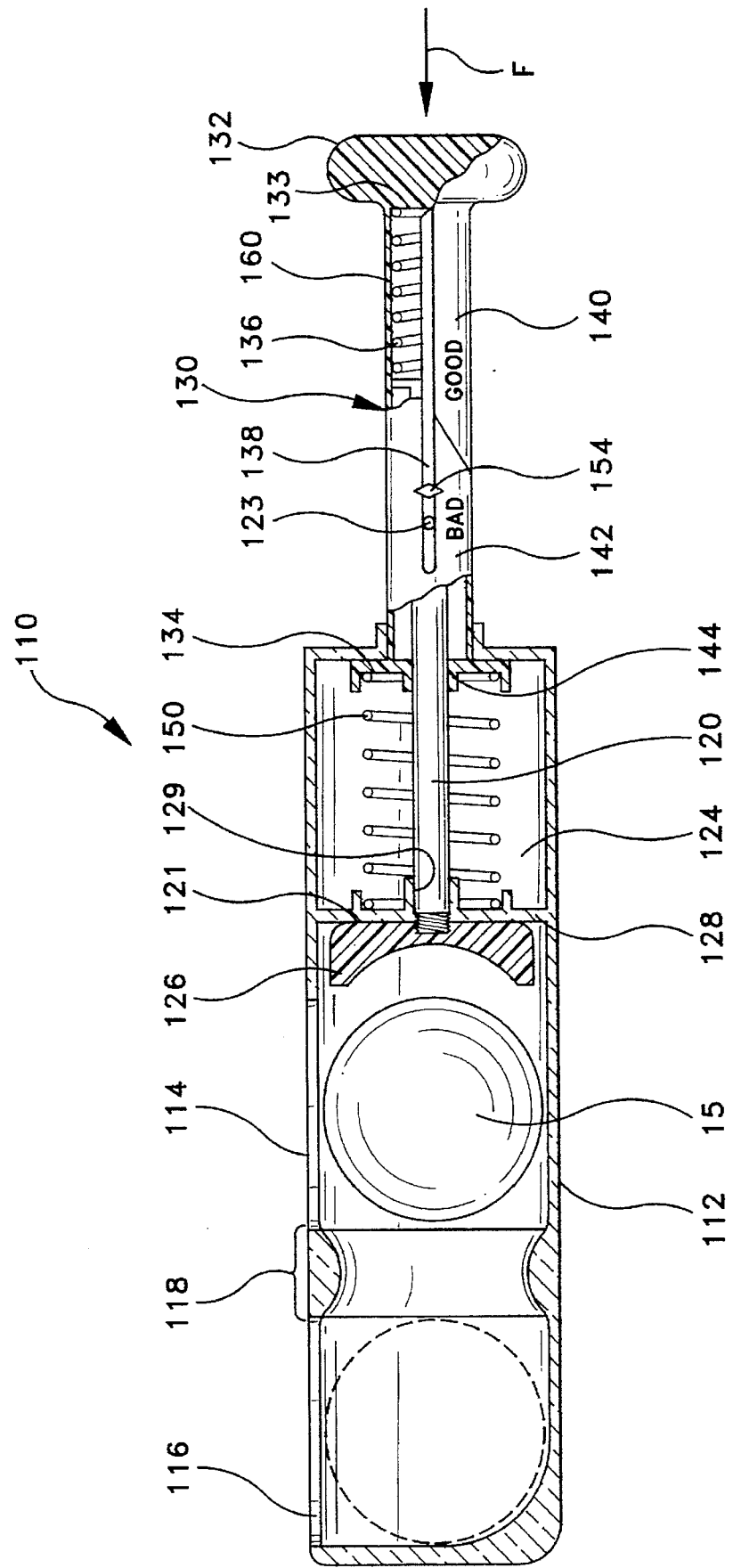
FIG. 2 is a selectively fragmented cross-sectional view of a second preferred embodiment of the present invention ball testing device, shown in conjunction with a tennis ball.

Referring to FIG. 2, there is shown an alternate embodiment of the present invention ball tester device 100. Like the previously explained embodiment, the shown embodiment has a tubular element 112 with two access ports 114, 116. A restricted region 118 is disposed between the two access ports 114, 116, wherein a test ball 15 passes through the restricted region 118 within the tubular element 112 during testing. A single guide rod 120 extends from the rear surface 121 of the ram head 126, wherein the guide rod 120 is concentric with the longitudinal axis of the tubular element 112.

A spring chamber 124 is defined by the distal end of the tubular element 112. The first wall 128 of the spring chamber 124 defines a central aperture 129 through which the guide rod 120 passes. The guide rod 120 is free to reciprocally move through the central aperture 129, but the first wall 128 aligns the guide rod 120 and holds it in a coaxial orientation within the longitudinal axis of the tubular structure 112. A plunger element 130 is provided for operating the ball tester device 100. The plunger element 130 terminates with a handle 132 at one end and a flange 134 at the opposite end. A tubular shaft 136 extends between the handle 132 and the flange 134. A slot 138 is formed along a length of the tubular shaft 136, wherein the slot 138 communicates with the hollow interior of the tubular shaft 136. A key projection 123 extends from guide rod 120 and projects into the slot 138. As such, when the plunger element 130 moves in relation to the guide rod 120, the key projection 123 moves within the slot 138. A gauge indicia is printed on the exterior of the tubular shaft 136 proximate the slot 138. The gauge indicia identifies portions of the slot 138 wherein a green colored "GOOD" section 140 is disposed near the handle 132 and a red colored "BAD" section 142 is disposed farther away from the handle 132.

The tubular shaft 136 of the plunger element 130 passes into the larger tubular element 112 through an aperture 144 in the end wall 145 of the tubular element 112. The flange 134 at the end of the tubular shaft 136 is disposed in the spring chamber 124 and prevents the tubular shaft 136 from being withdrawn out of the tubular element 112. The guide rod 120 extending from the rear of the ram head 126 passes into the plunger element 130 within the spring chamber 124. A return spring 150 is disposed between first wall 128 of the spring chamber 124 and the flange 134 at the end of the plunger element 130. As such, the flange 134 is biased away from the first wall 128 within the confines of the spring chamber 124.

A positional icon element 154 engages the slot 138 that is formed along the length of the tubular shaft 136. The icon element 154 extends through the slot 138 so as to be visible. The icon element 154 engages the slot 138 with some degree of friction. As such, although the icon element 154 is free to move back and forth along the length of the slot 138, a predetermined threshold force is needed to move the icon element 154. As will be explained, the icon element 154 is moved when the key projection 123 that extends into the slot 138 pushes against the icon element 154. Once such a positive pushing force is removed, the icon element 154 remains fixed in relation to the slot 138.

A compression spring 160 is positioned within the tubular shaft 136 of the plunger element 130. The compression spring 160 is disposed between the guide rod 120 and the interior end 133 of the tubular shaft 136. As such, the compression spring 160 provides a bias force that acts to separate guide rod 120 from the end of the tubular shaft 136 proximate the handle 132.

In operation, a test ball is placed into the tubular element 112 through the first access port 114. A force F is then applied to the handle 132 at the far end of the plunger element 130, thereby driving the plunger element 130 into the tubular element 112. As the plunger element 130 is advanced, the compression spring 160 becomes compressed and exerts a downward force on the guide rod 120. The downward force on the guide rod 120 is transferred to the ram head 126, thereby advancing the ram head 126 against the test ball 15. As the test ball 15 enters the restricted region 118, the force needed to advance the test ball 15 increases. Consequently, the compression spring 160 becomes more compressed as the resistance offered by the test ball 15 is overcome.

As the force F applied to the handle 132 increases, the compression spring 160 compresses and the plunger element 130 advances over the guide rod 120. As the plunger element 130 advances, the key protrusion 123 that extends from the guide rod 120, rides along the length of the slot 138. The key element 154, p engages the icon element 154, pushing the icon element 154 from the red colored "BAD" section 142, toward the green colored "GOOD" section 140.

As the plunger element 130 is advanced, the return spring 150 is also compressed against the first wall of the spring chamber 124. After the test ball 15 has been forced through the restricted region 118 and the manually applied force F is removed from the handle 132, the return spring 150 returns the plunger element 130 to its initial position by biasing the flange 134 the far end of the spring chamber 124. As a consequence, the plunger element 130 moves away from the guide rod 120 and the key projection 123 disengages the icon element 154. By viewing the position of the icon element 154 in the slot 138, the user of the ball tester 100 can ascertain what the maximum resistance force was supplied by the test ball 15. If the icon element 154 is positioned in the good section 140 of the slot 138, the test ball 15 is not too soft and can be used again. If the icon element 154 failed to leave the bad section 142 of the slot 138, the test ball 15 fails and can be discarded.

It will be understood that a person skilled in the art of presses could make alternate embodiments of the present invention using functionally equivalent components that have not been specifically described. For example, and an electronic gauge display could be used in place of the mechanical gauge described. Similarly, green and red lights could be used to indicate if a test ball tested properly or is too soft. All such obvious modifications are intended to be included in the scope of this disclosure as defined by the appended claims.

What is claimed is:

1. A ball testing device, comprising:
   a tubular element having an entrance port and an exit port both sized to enable the passage of said ball therethrough;
   a restricted region disposed within said tubular element between said entrance port and said exit port, wherein said restricted region defines an opening within said tubular element that is smaller than said ball;
   an advancement mechanism coupled to said tubular element for advancing said ball through said restricted region, wherein said ball resists being deformed through said restricted region with a predetermined force; and
   indicator means for providing an indication of whether said predetermined force surpasses a threshold value.

2. The device according to claim 1, wherein said advancement mechanism is manually powered.

3. The device according to claim 1, wherein said advancement mechanism includes a ramrod element having a first end that extends into said tubular element and a second end that extends from said tubular element, wherein said first end of said ramrod element abuts against and pushes said ball through said restricted region when a manual force greater than said predetermined force is applied to said second end of said ramrod element.

4. The device according to claim 3, wherein said advancement means includes a handle element and a spring disposed between said handle element and said ramrod element, wherein said spring compresses and transfers said manual force to said ramrod element when said manual force is applied to said handle element.

5. The device according to claim 4, wherein said indicator means includes a gauge that measures a change in length of said spring, between an initial spring length and a compressed spring length, as said spring compresses between said ramrod element and said handle element.

6. The device according to claim 5, further including an adjustment means for adjusting said initial spring length, thereby enabling said ball testing device to be selectively zeroed for a predetermined ball type.

7. The device according to claim 1, wherein said tubular element is transparent.

8. The device according to claim 1, wherein said indicator means includes a plurality of different gauge indicators, wherein each of said gauge indicators has a gauge indicia adapted for use with a specific type of ball type.

9. The device according to claim 4, wherein said first end of said ramrod element moves from a set position to an advanced position within said tubular element when said manual force is applied to said second end of said ramrod element, said device further including a return spring for returning said ramrod element to said set position after said manual force is removed from said second end of said ramrod element.

10. A method of testing a ball comprising the steps of:
    placing a ball on one side of a restriction;
    advancing said ball through said restriction wherein said ball resists being deformed through said restriction with a predetermined force;
    measuring said predetermined force; and
    comparing said predetermined force to a threshold value, wherein the failure of said predetermined force to surpass said threshold value is indicative of a rejectionable ball.

11. The method according to claim 10, wherein said step of advancing said ball through said restriction includes biasing a ramrod element against said ball.

12. The method according to claim 11, wherein said step of advancing said ball through said restriction further includes manually applying a force to a handle element coupled to said ramrod element with a spring, wherein said force is transferred to said ramrod element through said spring, thereby causing said spring to compress by a predetermined degree.

13. The method according to claim 12, wherein said step of measuring said predetermined force includes measuring said predetermined degree of compression of said spring.

14. The method according to claim 10 further including the step of selecting said threshold value depending upon the type of knapping contained on the ball being tested.

* * * * *